United States Patent [19]
Takemoto et al.

[11] Patent Number: 5,856,579
[45] Date of Patent: *Jan. 5, 1999

[54] ADDUCT SALTS OF NOVEL SUBSTITUTED BENZYLAMINES AND A PROCESS FOR OPTICALLY RESOLVING THEM

[75] Inventors: Tadashi Takemoto; Toyoto Hijiya; Teruo Yonekawa, all of Kawasaki, Japan

[73] Assignee: Ajinomoto Co., Inc., Tokyo, Japan

[ * ] Notice: The term of this patent shall not extend beyond the expiration date of Pat. No. 5,629,450.

[21] Appl. No.: 732,860

[22] Filed: Oct. 15, 1996

[30] Foreign Application Priority Data

Nov. 29, 1995 [JP] Japan .................................. 7-310368
Dec. 20, 1995 [JP] Japan .................................. 7-331457

[51] Int. Cl.$^6$ .......................... C07C 209/00; C07B 57/00
[52] U.S. Cl. ............................. 564/425; 564/304
[58] Field of Search .................................. 564/304, 425

[56] References Cited

U.S. PATENT DOCUMENTS 3,028,430  4/1962  Gillingham .......................... 260/570.8
5,629,450  5/1997  Hijiya et al. ............................. 564/425

FOREIGN PATENT DOCUMENTS 0 688 760  12/1995  European Pat. Off. .

OTHER PUBLICATIONS

Database WPI, Derwent Publications, AN–94–163883, JP–06–107604, Apr. 19, 1994.

Journal of the American Chemical Society, vol. 73, No. 12, pp. 5782–5783, Dec. 24, 1951, H. D. DeWitt, et al., "N–Acylamino Acids, A New Class of Resolving Agents".

*Primary Examiner*—Allen J. Robinson
*Assistant Examiner*—Barbara Badio
*Attorney, Agent, or Firm*—Oblon, Spivak, McClelland, Maier & Neustadt, P.C.

[57] ABSTRACT

A process for optical resolution of a racemic substituted benzylamine is provided that involves reacting the racemic substituted benzylamine in a solvent with an optically active N-acyl-phenylalanine, -aspartic acid, or -glutamic acid, and separating the diastereomers formed by making use of the difference in the mutual solubilities of the two diastereomer salts which are generated therein.

15 Claims, No Drawings

ADDUCT SALTS OF NOVEL SUBSTITUTED BENZYLAMINES AND A PROCESS FOR OPTICALLY RESOLVING THEM

BACKGROUND OF THE INVENTION

1. Field of the Invention

The present invention relates to a process for the optical resolution of optically active substituted benzylamines and the adduct salt of the substituted benzylamine and an N-acyl-amino acid formed in the separation.

2. Discussion of the Background

Optically active substituted benzylamines are important materials as optical resolving agents to obtain optically active isomers from racemic carboxylic acids. In particular, α-arylalkylamines comprising a phenyl group and methyl or ethyl group are frequently used as optical resolving agents. S or R amines in which the aryl groups are derived from a variety of aromatic compounds are also, important raw materials for potent sweetener compounds, comprising aspartyl dipeptide derivatives represented by the formula (2) below and their salts,

wherein, $R^1$ represents $C_{1-6}$ alkyl or $C_{2-7}$ alkoxymethyl; $R^2$ represents phenyl, benzyl, cyclohexyl, or cyclohexylmethyl; structures containing C* have an (S) configuration if the $R^1$ is an alkyl group and (R) configuration if $R^1$ is an alkoxymethyl group. If R, is alkyl, X represents D-norleucine, D-leucine, D-isoleucine, D-alloisoleucine, D-threonine, D-0-methyl-threonine, D-allothreonine, D-0-methylallothreonine, D- or DL-furylglycine or a similar D-α-amino acid residue or a DL-α-amino acid residue, or a $C_{3-6}$ cyclic or acyclic α,α-dialkyl amino acid residue; if $R^1$ is an alkoxymethyl group, X represents D-alanine, D-α-amino butyric acid, D-norvaline, D-valine, D-norleucine, D-leucine, D-isoleucine, D-alloisoleucine, D-t-leucine, D-serine, D-0-methylserine, D-threonine, D-0-methylthreonine, D-allothreonine, D-0-methyl allothreonine, D-phenylglycine, D- or DL-furylglycine or a similar D-α-amino acid residue or DL-α amino acid residue, or a $C_{3-6}$ cyclic or acyclic α,α-dialkyl amino acid residue. L—Asp and X are bonded via an α-bonding. These potent sweeteners also include aspartyl dipeptide amide derivatives represented by the general formula (3) below and their salts

wherein, X represents D-alanine, D-α-amino butyric acid, D-norvaline, D-valine, D-norleucine, D-leucine, D-isoleucine, D-alloisoleucine, D-t-leucine, D-serine, D-0-methylserine, D-threonine, D-0-methylthreonine, D-allothreonine, D-0-methylallothreonine, D-phenylglycine, D-or DL-furylglycine or a similar D-α-amino acid residue or DL-α-amino acid residue, or a $C_{3-6}$ cyclic or acyclic α,α-dialkyl amino acid residue; $R^1$ represents a $C_{1-6}$ alkyl group or $C_{2-7}$ alkoxymethyl group; $R^2$ represents a phenyl group having a substituent in the 2-, 3-, or 4- position selected from the group containing F, Cl, Br, I, hydroxy, $C_{1-6}$ alkoxy, cyano, nitro, acetyl, amino, and acetyl amino, or a phenyl group having a 2, 3- or 3, 4-methylenedioxy, trimethylene, or tetramethylene substituent; or 2, 3, or 4-pyridyl, 2- or 3-furyl, or 2- or 3-thienyl substituent; structures containing C* are (S) or (RS) isomers if $R^1$ is alkyl; or they represent (R), (S), or (RS) if $R^1$ is alkoxymethyl; and the L—Asp is bonded to X via an α-bonding.

Aspartyl dipeptides of formula (2) include α-L-aspartyl-D-threonine (S)-α-ethylbenzylamide; α-L-aspartyl-DL-furylglycine (S)-α-ethylbenzylamide; α-aspartyl-DL-furylglycine (S)-α-methoxymethylbenzylamide; α-L-aspartyl-α-aminocyclopentanecarboxylic acid (S)-α-ethylbenzylamide; α-L-aspartyl-aminocyclohexanecarboxylic acid (S)-α-ethylbenzylamide; α-L-aspartyl-D-valine (R)-α-methoxymethylbenzylamide; α-L-aspartyl- D-α-aminobutyric acid (R)-α-methoxymethylbenzylamide; and the like: Japanese Patent Application H7-42818.

Aspartyl dipeptide amides of formula (3) include α-L-aspartyl-D-α-aminobutyric acid (S)-α-ethyl-p-hydroxybenzylamide; α-L-aspartyl-D-α-aminobutyric acid (R)-methoxymethyl-p-hydroxybenzylamide; α-L-aspartyl-D-valine (S)-α-ethyl-p-hydroxybenzylamide; α-L-aspartyl-D-valine-(R)-α-methoxymethyl-p-hydroxybenzylamide; α-L-aspartyl-D-valine (S)-α-ethyl-p-chlorobenzylamide, and the like: Japanese Patent Application H7-144844.

Conventional methods for obtaining optically active substituted benzylamines from their racemic isomers by optical resolution generally call for forming salts with various optically active carboxylic acids and separating the two diastereomer salts generated by taking advantage of the difference in the solubilities. Methods are known in the art, for example, including a method which uses optically active tartaric acid or malic acid (J. Chem. Soc., 1940, 336), a method of using optically active N-acetyl-3,5-dibromo-tyrosine (J. Am. Chem. Soc., 73, 5782 (1951)), and a method of using optically active 2-benzamide cyclohexane carboxylic acid (Bull. Chem. Soc. Jpn., 61, 1395 (1988)).

However, methods in which tartaric acid and malic acids are used are low in optical refining efficiency, often requiring recrystallizing and refining the resultant diastereomer salts multiple times. Although tartaric acid and malic acid are relatively low in cost, they are difficult to efficiently recover in this resolution process, which is a problem for commercialization.

In the method using optically active N-acetyl-3,5-dibromo-tyrosine, the preparation of this material itself is cumbersome and provides only insufficient optical refining capability.

The use of optically active 2-benzamide-cyclohexane carboxylic acids often gives high optical purity amines in a single crystallization, but the crystallization yield is not very high. In addition this material is relatively expensive.

Thus, while these known resolving agents are excellent on a laboratory scale, all suffer from some problem when used in industrial scale.

SUMMARY OF THE INVENTION

Accordingly, an object of the present invention is to provide an efficient and low cost commercial process for manufacturing optically active substituted benzylamines by optical resolution of racemic substituted benzylamines.

This and other objects of the present invention have been satisfied by the discovery that mixing a racemic substituted benzylamine with an optically active N-acyl-phenylalanine (hereafter abbreviating phenylalanine as Phe) an optically active N-acyl-aspartic acid (hereafter abbreviating aspartic acid as Asp), or with an N-acyl-glutamic acid (hereafter abbreviating glutamic acid as Glu) in a suitable solvent results in precipitating a salt of the optically active N-acyl-Phe (N-acyl-Asp or N-acyl-Glu) with the optically active substituted benzylamine, with high resolution efficiency.

DETAILED DESCRIPTION OF THE PREFERRED EMBODIMENTS

The present invention relates to a process for optical resolution of a racemic substituted benzylamine comprising mixing a racemic substituted benzylamine with an optically active N-acyl-Phe (or -Asp or -Glu) in a suitable solvent to provide (1) a salt of the (R)-amine with the optically active N-acyl-Phe (or -Asp or -Glu) and (2) a salt of the (S)-amine with the optically active N-acyl-Phe (or -Asp or -Glu), i.e., two diastereomer salts; and using the difference in the solubilities of these diastereomer salts to separate the more insoluble diastereomer salt by crystallization, i.e., by optical resolution, followed by treatment with alkali, for easy isolation at high purity of the optically active substituted benzylamines.

The acyl groups for the optically active N-acyl-Phe, -Asp, or -Glu in this invention include acetyl, benzyloxycarbonyl, benzoyl, benzenesulfonyl, p-toluene sulfonyl, (hereafter abbreviated as Ac, Z, Bz, Bs, and Ts, respectively). These compounds can be readily prepared in high yield by conventional methods, such as the treatment with the corresponding acyl chloride, (such as benzyloxycarbonyl chloride, benzoyl chloride, etc.) with the optically active amino acid by a Schotten-Baumann reaction.

The optically active Phe, Asp, and Glu, which are starting materials for resolution agents may be either D- or L-isomers. The isomer used should be selected depending upon the desired optical isomer of the substituted benzylamine to be isolated. In particular, L—Asp and —Glu are commercially produced readily and at a low cost by the enzyme or fermentation process.

The substituted benzylamines which are mixed with the optically active N-acyl-amino acids include the optically active α-methoxymethylbenzylamine, or a (α-substituted phenyl) alkylamine or α-(substituted phenyl) alkoxyethylamine. The substituted benzylamines preferably being those represented by the formula (1)

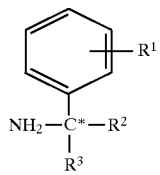

(1)

wherein $R^1$ represents a substituent in the 2-, 3-, or 4-position selected from the group consisting of F, Cl, Br, I, hydroxy, protected hydroxy, $C_{1-6}$ alkoxy, cyano, nitro, acetyl, amino, and acetylamino, $R^2$ and $R^3$ represent hydrogen or $C_{1-6}$ alkyl or $C_{2-7}$ alkoxymethyl (wherein $R^2 \neq R^3$), and C* is an asymmetric carbon.

Groups attached to the asymmetric carbon of the substituted benzylamine include phenyl, p-benzyloxy phenyl, and p-chlorophenyl as aryl groups, and other groups, such as methyl, ethyl, n-propyl, n-butyl, i-butyl, methoxymethyl, and ethoxymethyl.

Solvents which are preferred include water or hydrophilic organic solvents (for example, alcohols such as methanol and ethanol; ketones such as acetone and methylethylketone; ethers such as tetrahydrofuran, and dioxane; acetonitrile; N,N-dimethylformamide; and N,N-dimethylsulfoxide;) or a mixed solvent thereof.

The temperature at which the N-acyl-Phe, -Asp, or -Glu is mixed with the substituted benzylamine should not be higher than the boiling point of the solvent. The temperature is preferably in the range of 0°–100° C., more preferably in the range of 0°–80° C. The temperature of crystallization is preferably not higher than 60° C. for high yields, more preferably not higher than 50° C.

The amount of the optically active N-acyl-Phe, Asp, or -Glu used as a resolving agent should be 0.2–4 moles, preferably 0.3–1.5 moles, per mole of the racemic substituted benzylamine.

When the objective is precipitating the desired optical isomer amine as an insoluble salt with the N-acyl-Phe, -Asp, or -Glu and to remove the other optical isomer amine as a highly soluble hydrochloride salt in the mother liquor, it is preferred to also add an acid, such as hydrochloric acid, to the racemic amine for crystallization.

The racemic substituted benzylamine to be resolved does not necessarily have to be an equimolar mixture of R and S isomers and a mixture containing either isomer in an amount more than equimolar may be used.

The diastereomer salt obtained by crystallization can optionally be recrystallized or treated by a similar method to further increase the optical purity of the optically active amine.

After the desired diastereomer salt is obtained, it can be decomposed by a suitable method to isolate the optically active amine and the resolving agent.

Any conventional method can be used to decompose the diastereomer salt. For example, an aqueous solution containing the diastereomer salt can be made alkaline and the optically active amine extracted with a suitable organic solvent which separates it from the water layer. Distilling off the organic solvent thus provides the optically active amine. In addition, after extraction of the amine, the aqueous layer may be made acidic, followed by extracting with a suitable solvent and distilling off the organic solvent to isolate the N-acyl-amino acid. The N-acyl-amino acid is then recyclable as a resolving agent.

Having generally described this invention, a further understanding can be obtained by reference to certain specific examples which are provided herein for purposes of illustration only and are not intended to be limiting unless otherwise specified.

EXAMPLE

The optical purity of the substituted benzylamines were determined using an optically active HPLC column (Crown Pack CR (+)).

EXAMPLE 1

0.38 g (2.5 mmoles) of (R)-α-methoxymethylbenzylamine and 0.67 g (2.5 mmoles) of Z—L—Asp were added to 3 mL of water and dissolved by heating to 60° C. To a syrup obtained by concentrating the solution at reduced pressure was added 5 mL of ethyl acetate, followed by allowing the solution to stand for one hour at room temperature. The precipitated crystals were separated by suction filtration, rinsed with a small amount of ethyl acetate, and then vacuum dried. The weight of the crystals was 0.84 g. An HPLC analysis showed these crystals contained 516 mg (1.93 mmoles) of Z—L—Asp and 321 mg (2.12 mmoles) of (R)-α-methoxymethylbenzylamine.

EXAMPLE 2

0.38 g (2.5 mmoles) of (R)-α-methoxymethylbenzylamine and 0.63 g (2.5 mmoles) of Bz—L—Glu were added to 3 mL of water and dissolved by heating to 60° C. To a syrup obtained by concentrating this solution at reduced pressure was added 10 mL of isopropyl alcohol, followed by concentrating at reduced pressure. 10 mL of ethyl acetate was added to the resulting crystals and the crystals separated by suction filtration. The crystals were rinsed with a small amount of ethyl acetate, and then vacuum dried. The weight of the crystals was 0.86 g. An HPLC analysis showed that these crystals contained 516 mg (2.05 mmoles) of Bz—L—Glu and 344 mg (2.27 mmoles) of (R)-α-methoxymethylbenzylamine.

EXAMPLE 3

0.38 g (2.5 mmoles) of (R)-α-methoxymethylbenzylamine and 0.75 g (2.5 mmoles) of Ts—L—Glu were added to 3 mL of water and dissolved by heating to 60° C. To a syrup obtained by concentrating this solution at reduced pressure was added 30 mL of hexane, and crystallized by abrasion with a spatula. After concentrating at reduced pressure, 10 mL of ethyl acetate was added to the solution and the precipitated crystals were separated by suction filtration. The crystals were rinsed with a small amount of ethyl acetate and then vacuum dried. The weight of the crystals was 0.58 g. An HPLC analysis showed that these crystals contained 375 mg (1.24 mmoles) of Ts—L—Glu, 207 mg (1.37 mmoles) of (R)-α-methoxymethylbenzylamine.

EXAMPLE 4

0.38 g (2.5 mmoles) of (R)-α-methoxymethylbenzylamine and 0.70 g (2.5 mmoles) of Z—L—Glu were added to 10 mL of ethyl acetate and dissolved by heating to 50° C., followed by allowing the solution to stand for 4 hours at room temperature. The precipitated crystals were separated by suction filtration, rinsed with a small amount of ethyl acetate, and then vacuum dried. The weight of the crystals was 0.86 g. An HPLC analysis showed that these crystals contained 535 mg (1.90 mmoles) of Z—L—Glu and 322 mg (2.13 mmoles) of (R)-α-methoxymethylbenzylamine.

EXAMPLE 5

0.38 g (2.5 mmoles) of (R)-α-methoxymethylbenzylamine and 0.72 g (2.5 mmoles) of Bs—L—Glu were added to 3 mL of water and dissolved by heating to 60° C. To a syrup obtained by concentrating this solution was added 30 mL of hexane, and crystallized by abrasion with a spatula while cooling with ice. After concentrating at reduced pressure, 10 mL of ethyl acetate was added, and the precipitated crystals were separated by suction filtration. The crystals were rinsed with a small amount of ethyl acetate, and then vacuum dried. The weight of the crystals was 0.90 g. An HPLC analysis showed that these crystals contained 578 mg (2.01 mmoles) of Bs—L—Glu and 325 mg (2.15 mmoles) of (R)-α-methoxymethylbenzylamine.

EXAMPLE 6

0.38 g (2.5 mmoles) of (R)-α-methoxymethylbenzylamine and 0.52 g (2.5 mmoles) of Ac—L—Phe were added to aqueous methanol (13 mL of water+7 mL of methanol) and dissolved by heating to 60° C. The solution was allowed to settle overnight in a refrigerator and the precipitated crystals were separated by suction filtration. The crystals were rinsed with a small amount of cold water, and then vacuum dried. The weight of the crystals was 0.71 g. An HPLC analysis showed these crystals contained 394 mg (1.90 mmoles) of Ac—L—Phe, and 316 mg (2.09 mmoles) of (R)-α-methoxymethylbenzylamine.

EXAMPLE 7

0.26 g (1.0 mmoles) of (R)-α-methoxymethyl-p-benzyloxybenzylamine and 0.27 g (1.0 mmoles) of Z—L—Asp were added to 3 mL of methanol and dissolved by heating to 40° C. The solution was allowed to stand for 30 minutes at room temperature. The precipitated crystals were separated by suction filtration followed by rinsing with a small amount of cold methanol, and then vacuum dried. The weight of the crystals was 0.45 g. The crystals were dissolved in 30 mL of methanol. 0.15 g of 5% Pd-carbon with 50% water content and 0.1 mL of acetic acid were added to the solution and reduced for 4 hours at 50° C. under an atmosphere of hydrogen. The catalyst was removed by filtration and the filtrate was concentrated at reduced pressure. An HPLC analysis of the residue showed that 109 mg (0.82 mmoles) of L—Asp and 150 mg (0.90 mmoles) of (R)-α-methoxymethyl-p-hydroxybenzyiamine were contained.

EXAMPLE 8

0.77 g (5.1 mmoles) of (RS)-α-methoxymethylbenzylamine and 0.70 g (2.55 mmoles) of Z—L—Glu were added to 4 mL of water. To this solution was added 0.83 mL (2.5 mmoles) of 3 N-HCl. The solution was allowed to stand overnight at 5° C. and the precipitated crystals were separated by suction filtration. The weight of the wet crystals was 846 mg. An HPLC analysis showed these crystals to contain 280 mg (0.99 mmoles) of Z—L—Glu, 133 mg (0.88 mmoles) of (R)-α-methoxymethylbenzylamine, and 25.2 mg (0.17 mmoles) of (S)-α-methoxymethylbenzylamine. The yield of the R-isomer was 34.3% with respect to the R-isomer amine charged; optical purity was 68.0% ee.

EXAMPLE 9

0.78 g (5.1 mmoles) of (RS)-α-methoxymethylbenzylamine and 0.75 g (2.5 mmoles) of Ts—L—Glu were added to 4 mL of water. To this solution was added 0.83 mL (2.5 mmoles) of 3 N-HCl. The solution was allowed to stand overnight at 5° C. and the precipitated crystals were separated by suction filtration. The weight of the wet crystals was 563 mg. An HPLC analysis showed these crystals to contain 231 mg (0.77 mmoles) of Ts—L—Glu, 174 mg (1.15 mmoles) of (R)-α-methoxymethylbenzylamine, and 29.4 mg (0.19 mmoles) of (S)-α-methoxymethylbenzylamine. The yield of the R-isomer was 44.7% with respect to the R-isomer amine charged; optical purity was 71.1 % ee.

EXAMPLE 10

0.76 g (5.0 mmoles) of (RS)-α-methoxymethylbenzylamine and 0.63 g (2.5 mmoles) of Bz—L—Glu were added to 4 mL of water. To this solution was added 0.83 mL (2.5 mmoles) of 3 N-HCl. The solution was allowed to stand overnight at 5° C. and the precipitated crystals were separated by suction filtration. The weight of the wet crystals was 588 mg. An HPLC analysis showed these crystals to contain 347 mg (1.38 mmoles) of Bz—L—Glu, 193 mg (1.28 mmoles) of (R)-α-methoxymethylbenzylamine, and 24.9 mg (0.17 mmoles) of (S)-α-methoxymethylbenzylamine. The yield of the R-isomer was 51.8% with respect to the R-isomer amine charged; optical purity was 77.2% ee.

EXAMPLE 11

0.76 g (5.0 mmoles) of (RS)-α-methoxymethylbenzylamine and 0.72 g (2.5 mmoles) of Bs—L—Glu were added to 4 mL of water. To this solution was added 0.83 mL (2.5 mmoles) of 3 N-HCl. The solution was allowed to stand overnight at 5° C. and the precipitated crystals were separated by suction filtration. The weight of the wet crystals was 181 mg. An HPLC analysis showed these crystals to contain 110 mg (0.38 mmoles) of Bs—L—Glu, 52.8 mg (0.35 mmoles) of (R)-α-methoxymethylbenzylamine, and 12.6 mg (0.083 mmoles) of (S)-α-methoxymethylbenzylamine. The yield of the R-isomer was 14.0% with respect to the R-isomer amine charged; optical purity was 61.5% ee.

EXAMPLE 12

0.76 g (5.0 mmoles) of (RS)-α-methoxymethylbenzylamine and 1.04 g (5.0 mmoles) of Ac—L—Phe were added to aqueous methanol (24 mL of water+15 mL of methanol) and dissolved by heating to 60° C. The solution was allowed to stand overnight at 5° C. and the precipitated crystals were separated by suction filtration. The weight of the wet crystals was 0.45 g. An HPLC analysis showed these crystals to contain 236 mg (1.14 mmoles) of Ac—L—Phe, 196 mg (1.29 mmoles) of (R)-α-methoxymethylbenzylamine, and 6.1 mg (0.040 mmoles) of (S)-α-methoxymethylbenzylamine. The yield of the R-isomer was 51.8% with respect to the R-isomer amine charged; optical purity was 93.9% ee.

EXAMPLE 13

1.51 g (10 mmoles) of (RS)-α-methoxymethylbenzylamine and 1.44 g (5.0 mmoles) of Ts—L—Asp were added to 8 mL of water. To this solution was added 1.67 mL (5.0 mmoles) of 3 N-HCl. The solution was stirred for one hour at room temperature and the precipitated crystals were separated by suction filtration. The weight of the wet crystals was 4.50 g. An HPLC analysis showed these crystals to contain 1.32 g (4.60 mmoles) of Ts—L—Asp, 633 mg (4.19 mmoles) of (S)-α-methoxymethylbenzylamine, and 268 mg (1.77 mmoles) of (R)-α-methoxymethylbenzylamine. The yield of the S-isomer was 83.7% with respect to the S-isomer amine charged; optical purity was 40.5% ee.

EXAMPLE 14

151.2 g (1.0 moles) of (RS)-α-methoxymethylbenzylamine and 125.6 g (0.5 moles) of Bz—L—Glu were added to 700 mL of water, followed by heating to 60° C. To the solution was added 167 mL (0.5 moles) of 3 N-HCl. The solution was allowed to stand overnight at 5° C. and the precipitated crystals were separated by suction filtration. The weight of the wet crystals was 138.3 g. An HPLC analysis showed these crystals to contain 67.8 g (0.27 moles) of Bz—L—Glu, 38.2 g (0.25 moles) of (R)-α-methoxymethylbenzylamine, and 4.6 g (0.030 moles) of (S)-α-methoxymethylbenzylamine. The yield of the R-isomer was 50.5% with respect to the R-isomer amine charged; optical purity was 78.3% ee.

100 g of the wet crystals were dissolved by heating in 3,000 mL of water to 60° C. Trace insolubles were removed by filtration and the filtrate was allowed to stand overnight at 5° C. for recrystallization. The precipitated crystals were separated by suction filtration. The weight of the wet crystals was 65.3 g. An HPLC analysis showed these crystals to contain 18.9 g of (R)-α-methoxymethyl benzylamine and 0.60 g of (S)-α-methoxymethylbenzylamine. The R-amine isomer recrystallization yield was 50.1%; optical purity was 93.8% ee.

60 g of these crystals were dispersed in 150 mL of water followed by adding 25% NaOH to bring the pH of the solution to 12 followed by extracting twice with 200 mL portions of ether. The ether layers were collected, rinsed with saturated brine, and dried over anhydrous sodium sulfate. The sodium sulfate was removed by filtration and the ether was distilled off from the filtrate at reduced pressure to give 16.8 g of oily (R)-α-methoxymethylbenzylamine. The yield from the R-isomer in the starting material (RS)-amine was 22.2%.

As shown above, the process of the present invention permits an optical resolution of a substituted benzylamine at a high yield by a simple operation using a low cost material as a resolving agent.

This application is based on Japanese Patent Applications 310368/1995 and 331457/1995, filed with the Japanese Patent Office on Nov. 29, 1995 and Dec. 20, 1995, respectively, the entire contents of each of which are hereby incorporated by reference.

Obviously, additional modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for optically resolving a substituted benzylamine comprising:

reacting, in a solvent, a racemic substituted benzylamine selected from the group consisting of racemic α-methoxymethylbenzylamines, racemic α-(substituted phenyl)alkylamines and racemic α-(substituted phenyl)alkoxyethylamines, with an optically active N-acyl-phenylalanine, -aspartic acid, or -glutamic acid at a temperature sufficient to effect formation of two diastereomeric salts; and separating said diastereomeric salts by making use of differences in mutual solubilities of said two diastereomeric salts by selective precipitation of the less soluble of the two diastereomeric salts.

2. The process as claimed in claim 1, wherein said racemic substituted benzylamine is a compound of formula (1)

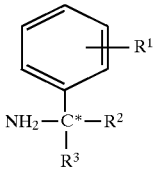

(1)

wherein $R^1$ is a substituent in a 2-, 3-, or 4-position selected from the group consisting of F, Cl, Br, I, hydroxy, protected hydroxy, $C_{1-6}$ alkoxy, cyano, nitro, acetyl, amino, and acetylamino; $R^2$ and $R^3$ each, independently, is hydrogen or $C_{1-6}$ alkyl or $C_{2-7}$ alkoxymethyl, with the proviso that $R^2 \neq R^3$ thus making C* an asymmetric carbon.

3. The process as claimed in claim 1, wherein said optically active N-acyl-phenylalanine, -aspartic acid, or -glutamic acid has an acyl group selected from the group consisting of acetyl, benzyloxycarbonyl, benzoyl, benzenesulfonyl and p-toluenesulfonyl.

4. The process as claimed in claim 1, wherein said racemic substituted benzylamine is (RS)-α-methoxymethyl benzylamine and said N-acyl-phenylalanine is N-acetyl-L-phenylalanine.

5. The process as claimed in claim 1, wherein said racemic substituted benzylamine is (RS)-α-methoxymethyl-p-benzyloxybenzylamine and said N-acyl aspartic acid is N-benzyloxycarbonyl-L-aspartic acid.

6. The process as claimed in claim 1, wherein said temperature is in a range of from 0° to 100° C.

7. The process as claimed in claim 1, wherein said temperature is in a range of from 0° to 80° C.

8. The process as claimed in claim 1, wherein said solvent is a member selected from the group consisting of water, hydrophilic organic solvents and mixtures thereof.

9. The process as claimed in claim 8, wherein said hydrophilic organic solvent is a member selected from the group consisting of alcohols, ketones, ethers, acetonitrile, N,N-dimethylformamide, dimethylsulfoxide and mixtures thereof.

10. The process as claimed in claim 1, wherein said optically active N-acyl-phenylalanine, N-acyl-aspartic acid or N-acyl-glutamic acid is present in an amount of from 0.2 to 4 moles per mole of said racemic substituted benzylamine.

11. The process as claimed in claim 1, wherein said optically active N-acyl-phenylalanine, N-acyl-aspartic acid or N-acyl-glutamic acid is present in an amount of from 0.3 to 1.5 moles per mole of said racemic substituted benzylamine.

12. The process as claimed in claim 1, wherein in said separating step, an inorganic acid is added to aid in precipitation of said least soluble of said two diastereomeric salts.

13. The process as claimed in claim 12, wherein said inorganic acid is hydrochloric acid.

14. The process as claimed in claim 1, wherein said racemic substituted benzylamine is an equimolar mixture of R and S isomers.

15. The process as claimed in claim 1, further comprising, after said separation step, a step of decomposing said least soluble of the two diasteriomeric salts to provide an optically enriched substituted benzylamine and recover said optically active N-acyl-phenylalanine, N-acyl-aspartic acid or N-acyl-glutamic acid.

* * * * *